(12) United States Patent
Kruijsen et al.

(10) Patent No.: US 7,597,672 B2
(45) Date of Patent: Oct. 6, 2009

(54) HIP ORTHOSIS, METHOD FOR PREVENTING THE DISLOCATION OF A HIP AND USE OF A HIP ORTHOSIS

(75) Inventors: Lambertus Joseph Martinus Kruijsen, Uden (NL); Gert Nijenbanning, Oldenzaal (NL)

(73) Assignee: Össur Europe B.V., Reykjavik (IS)

( * ) Notice: Subject to any disclaimer, the term of this patent is extended or adjusted under 35 U.S.C. 154(b) by 315 days.

(21) Appl. No.: 11/438,474

(22) Filed: May 22, 2006

(65) Prior Publication Data

US 2006/0264790 A1 Nov. 23, 2006

(30) Foreign Application Priority Data

May 20, 2005 (NL) .................................. 1029086

(51) Int. Cl.
*A61F 5/00* (2006.01)
*A61F 5/24* (2006.01)
*A61F 5/30* (2006.01)
*A61F 13/00* (2006.01)
*A61F 5/37* (2006.01)
*A61B 19/00* (2006.01)

(52) U.S. Cl. ............... 602/16; 602/5; 602/23; 602/24; 128/95.1; 128/117.1; 128/846; 128/869; 128/882

(58) Field of Classification Search ........ 602/5, 602/12, 16, 19, 23, 24; 128/95.1, 96.1, 98.1, 128/106.1, 108.1, 112.1, 117.1, 119.1, 845, 128/846, 869, 882; 623/31–38
See application file for complete search history.

(56) References Cited

U.S. PATENT DOCUMENTS

| 4,905,678 | A | * | 3/1990 | Cumins et al. ................ 602/16 |
| 5,368,552 | A | | 11/1994 | Williamson et al. |
| 5,620,412 | A | | 4/1997 | Modglin |
| 5,840,050 | A | * | 11/1998 | Lerman ....................... 602/19 |
| 5,938,629 | A | * | 8/1999 | Bloedau ...................... 602/16 |
| 6,027,466 | A | | 2/2000 | Diefenbacher et al. |
| 6,039,707 | A | * | 3/2000 | Crawford et al. ............... 602/5 |
| 6,090,057 | A | | 7/2000 | Collins et al. |
| 6,540,703 | B1 | | 4/2003 | Lerman |
| 2003/0229301 | A1 | | 12/2003 | Coligado |
| 2004/0024340 | A1 | | 2/2004 | Schwenn |
| 2004/0116260 | A1 | | 6/2004 | Drennan |

FOREIGN PATENT DOCUMENTS

| DE | G8804683.4 | 7/1988 |
| EP | 0 657 149 | 6/1995 |
| EP | 1 159 940 | 12/2001 |

* cited by examiner

*Primary Examiner*—Patricia M Bianco
*Assistant Examiner*—Brandon Jackson
(74) *Attorney, Agent, or Firm*—Bacon & Thomas, PLLC (57) ABSTRACT

A hip orthosis, provided with a trunk engaging part and an upper leg engaging part which are intercoupled by coupling means, wherein the coupling comprise at least one resilient element for operatively preventing an adducting movement of an upper leg engaged by the upper leg engaging part by means of spring force.

27 Claims, 5 Drawing Sheets

HIP ORTHOSIS, METHOD FOR PREVENTING THE DISLOCATION OF A HIP AND USE OF A HIP ORTHOSIS

The invention relates to a hip orthosis, provided with a trunk engaging part and an upper leg engaging part which are intercoupled by coupling means.

The invention further relates to a method for preventing the dislocation of a hip.

The invention further relates to the use of a hip orthosis according to the invention, for preventing the dislocation of a hip, for instance during recovery from hip surgery.

Many forms of surgery of a hip joint or an upper part of the thigh require an incision in the muscles and/or tendons near the hip joint of a patient. These muscles and tendons provide the movement of the hip, but also ensure that the hip ball is kept in its socket. During the recovery from hip surgery, the muscles and tendons will be weakened and will, in many cases, not be able to keep the hip ball in its socket. After hip surgery, there is therefore an increased risk of a hip coming out of its socket (hip dislocation). In addition to causing severe pain, such a hip dislocation may make it necessary for the patient to have surgery again in order to place the hip ball in its socket.

A hip orthosis for preventing the dislocation of a hip is known from American patent publication. U.S. Pat. No. 6,540,703. The known hip orthosis is provided with an adjustable hinge which, in use, only allows rotation of the upper leg about the hip joint in forward and backward direction. This binge enables a person wearing a hip orthosis to move the upper leg with respect to the trunk about an axis of rotation of the hinge, so that the person can make a more or less normal walking movement. Here, the freedom of movement can be limited in an adjustable manner. The upper leg recedes outwards with respect to the trunk at a predetermined fixed angle for preventing the dislocation of the hip after, for instance, placement of a hip prosthesis.

The known hip orthosis has the drawback that, if the person is sitting or is going to sit, the trunk engaging part, which is arranged for engaging the trunk of the person in use, and the upper leg engaging part, which is arranged for engaging the upper leg of the person in use, can exert such forces on each other that the orthosis tends to twist around the trunk, so that correct positioning of the upper leg with respect to the trunk is not guaranteed. In addition, in order to prevent twisting, the known hip orthosis needs to be laced up very tightly around the trunk, which adversely affects the wearing comfort. In practice, this is often solved by a wearer of the orthosis by making the lacing looser, which cancels the effect of the orthosis.

It is an object of the invention to provide a hip orthosis which keeps the upper leg positioned correctly with respect to the trunk during use, while the orthosis has a great wearing comfort.

To this end, the invention provides a hip orthosis which is characterized in that the coupling means comprise at least one resilient element for operatively preventing an adducting movement of an upper leg engaged by the upper leg engaging part by means of spring force. Due to the resilient element, the orthosis is able to, operatively, exert a force and/or a moment on the upper leg which makes the upper leg abduct, viewed from the front side of the person, preferably independently of the position of the upper leg with respect to the trunk. In addition, the person has more freedom of movement, since the upper leg can thus preferably move in all directions and not only in one direction which is, for instance, determined by a hinge, while a desired interplay of forces can continue to act on the hip. This offers more comfort and, in addition, the possibility of m ore efficient exercise of the muscles around the hip joint, which muscles are weakened due to, for instance, surgery, in which a hip prosthesis has been placed. It is noted that the term 'adduction' can be defined as being a movement towards the trunk. The term 'abduction' can be defined as being a movement by which a body part is moved away from the axis of the body.

Preferably, in use, the at least one resilient element exerts a force on the hip joint, such that the hip is pressed into its socket under the influence of that force, so that the risk of dislocation is reduced further.

Preferably, in use, the at least one resilient element exerts a moment ion the hip joint. This allows the upper leg to be given a preferred position with respect to the trunk and/or to rotate it to a preferred position.

More preferably, in use, the moment is directed such that, under the influence of the moment, the upper leg is rotated substantially outwards, at least into a direction transverse to the sagittal plane. Thus, too great an abduction of the upper leg (towards the other leg), which increases the risk of dislocation of the hip, can be prevented.

Preferably, the coupling means comprise a connecting part connected with the upper leg engaging part and a coupling part connected with the trunk engaging part, while, during use, this connecting part is rotatable about a point of rotation with respect to this coupling part. This point of rotation is, for instance, a virtual point of rotation. Preferably, the orthosis, in particular the trunk engaging part, is designed such that, in use, the point of rotation is located on a line which intersects the two hip balls of a wearer of the orthosis. This offers the advantage that the freedom of movement of the upper leg is substantially not hindered with regard to a rotation about the hip ball.

Preferably, in use, the connecting part and the coupling part are pretensioned with respect to each other. This offers the advantage that the upper leg engaging part and the trunk engaging part can exert a force and/or moment on the hip joint in a simple manner.

Preferably, the connecting part comprises the resilient element, in particular a leaf spring, so that the orthosis can have a relatively inexpensive, compact and light design.

Preferably, it holds that, if the upper leg engaging part has been fitted to the upper leg, the leaf spring recedes away from the upper leg in unloaded condition and is tensioned along the upper leg in loaded condition.

This offers the advantage that, if the trunk engaging part has been fitted to the trunk in a simple manner, a force and optionally a moment can be applied around the hip joint.

Preferably, in use, the connecting part and the coupling part engage each other at least in a point of contact, which operatively moves with respect to the trunk engaging part if the upper leg is moved relative to the trunk. Preferably, in use, the point of contact is located at a distance from the point of rotation. Thus, in a simple manner, a moment can be applied around the hip joint. Varying the point of engagement offers the advantage that the direction of the moment on the hip joint can vary with respect to the trunk if the upper leg is moved relative to the trunk.

Preferably, in use, the connecting part reaches beyond the point of rotation, viewed in a direction from the upper leg engaging part towards the point of rotation. Preferably, the coupling part at least engages the portion of the connecting part reaching beyond the point of rotation, with different rotational positions of the connecting part. The advantage of this is that, at all times, irrespective of whether the person is walking, standing, sitting or lying, a moment can be exerted on the hip joint, which moment is directed such that the knee is pressed substantially outwards, at least in a direction transverse to the sagittal plane. Thus, too great an adduction of the upper leg, which increases the risk of dislocation of the hip, can be prevented.

Preferably, the connecting part is slidably coupled to the coupling part. Thus, the movement of the point of contact during the movement of the upper leg engaging part with respect to the trunk engaging part can be realized in a simple and inexpensive manner. In addition, thus, the upper leg engaging part substantially does not exert any force on the trunk engaging part in tangential or axial direction. This reduces the tendency of the trunk engaging part to twist around the trunk.

In one embodiment, the connecting part comprises a rod-shaped end and the coupling part is arranged for operatively preventing an outward movement of the rod-shaped end with respect to the trunk engaging part.

Thus, in a simple and inexpensive manner, a force and a moment can be applied to the hip joint.

In another embodiment, the connecting part comprises an annular end and the coupling part is arranged for operatively preventing an outward movement of the annular end with respect to the trunk engaging part. Thus, likewise, in a simple and expensive manner, a force and a moment can be applied to the hip joint.

The method according to the invention is characterized in that an inward movement of the associated upper leg is prevented by means of spring force. Preferably, the force is substantially directed such that the hip is pressed into its socket under the influence of that force. This further reduces the risk of dislocation. Preferably, the upper leg is rotated substantially outwards, in a direction transverse to the sagittal plane, by a moment. Thus, too great an adduction of the upper leg (towards the other leg), which increases the risk of dislocation of the hip, can be prevented. By these measures, movement of the upper leg in forward, backward and sideward direction is preferably not prevented. This offers more comfort and the possibility of more efficient exercise of the muscles around the hip joint, which muscles are weakened by, for instance, surgery, in which a hip prosthesis has been placed.

An example of a hip orthosis according to the invention will now be explained in more detail with reference to the drawings, in which.

Figure 1:
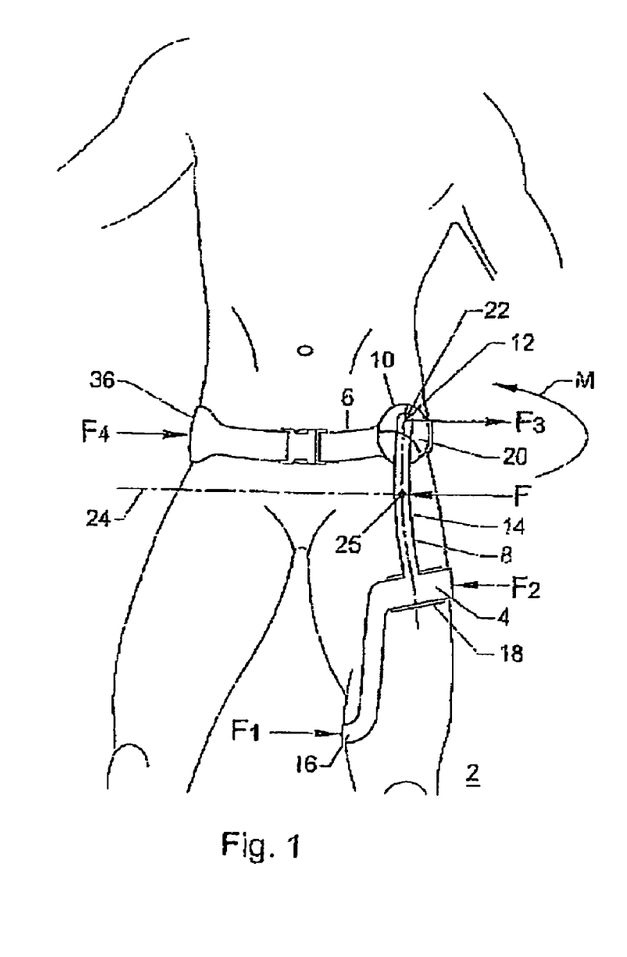
FIG. 1 shows a perspective front view of a first exemplary embodiment during use, when the wearer is standing.

FIG. 1 shows an embodiment of a hip orthosis 2 for preventing the dislocation of a hip according to the invention. In FIG. 1, the hip orthosis 2 has been fitted to a person in standing position. The orthosis 2 is provided with an upper leg engaging part 4, which is arranged for engaging an upper leg of the person, in use, and a trunk engaging part 6, which is arranged for engaging the trunk of the person, in use. The trunk engaging part 6 is provided with a trunk girding part 34 which girds the trunk during use. The upper leg engaging part 4 and the trunk engaging part 6 are intercoupled by means of coupling means 8, 10. The coupling means comprise a connecting part 8 connected with the upper leg engaging part 4 and a coupling part 10 connected with the trunk engaging part 6, which parts 8, 10 are rotatable with respect to each other during use. In the Figure, reference numeral 25 designates a virtual point of rotation, about which point of rotation the trunk engaging part 6 and upper leg engaging part 4 are rotatable with respect to each other. Here, the orthosis 2, in particular the trunk engaging part 6, is designed such that the virtual point of rotation 25 is, in use, substantially on a virtual line 24 which intersects the two hip balls of the wearer of the orthosis. The connecting part 8 reaches beyond the point of rotation 25, viewed in a direction from the upper leg engaging part 4 towards the point of rotation 25. The coupling part 10 engages the portion of the connecting part 8 reaching beyond the point of rotation 25. The connecting part 8 and the coupling part 10 engage with respect to each other in a point of contact 12.

In FIG. 1, the connecting part 8 is provided with a resilient element 14. In the embodiment shown, the resilient element 14 comprises a leaf spring from, for instance, metal or plastic. Due to the resilient element 14, the orthosis is capable of, operatively, exerting a force and/or a moment on the upper leg which makes the upper leg abduct, viewed from the front side of the person, preferably independently of the position of the upper leg with respect to the trunk. In addition, the person has more freedom of movement, since the upper leg can preferably move in all directions. This offers more comfort and the possibility of more efficient exercise of the muscles around the hip joint, which muscles are weakened by, for instance, surgery.

Figure 6A:
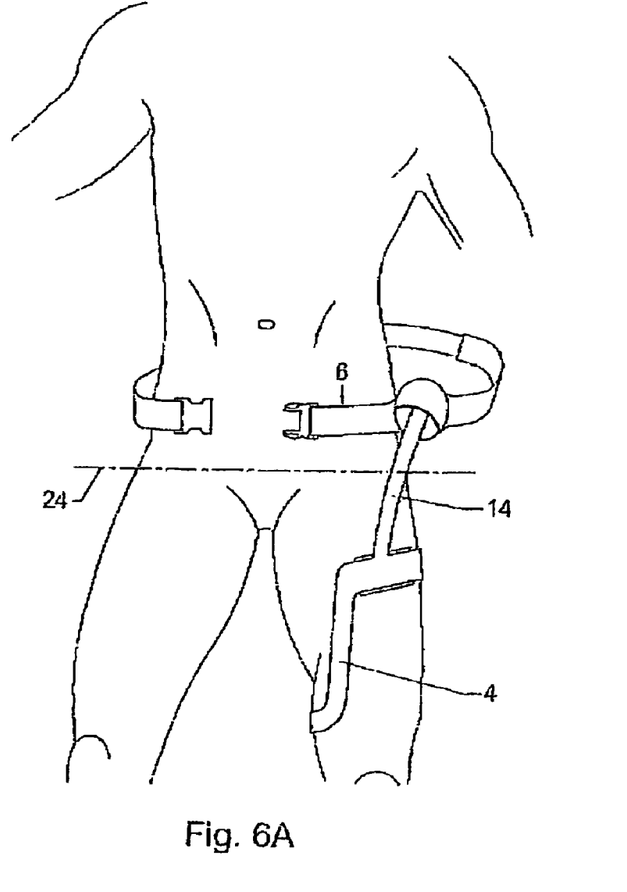
FIG. 6a shows a similar view to FIG. 1 of the first exemplary is embodiment in untensioned condition.
Figure 6B:
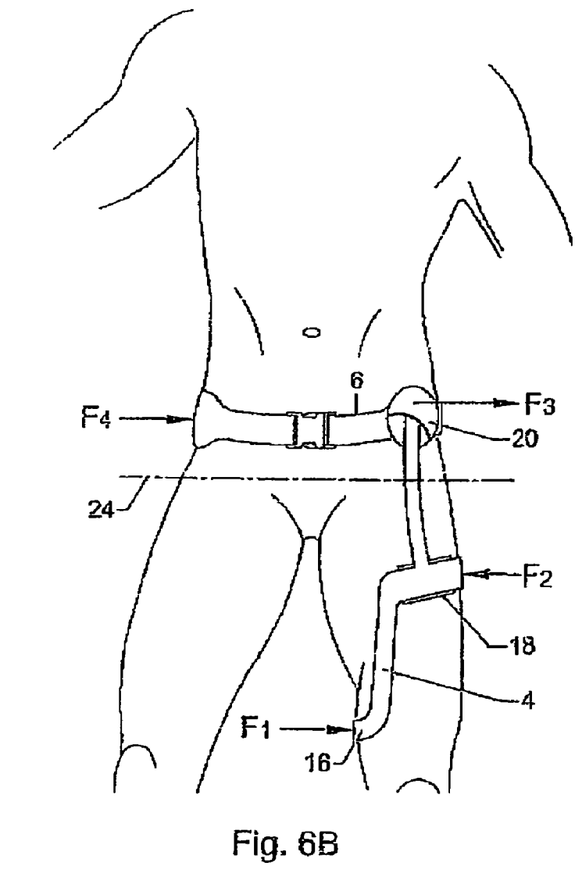
FIG. 6b shows the orthosis of FIG. 6a in tensioned condition.

In use, the resilient element 14 exerts a force on the upper leg engaging part 4 and the trunk engaging part 6, so that the connecting part 8 and the coupling part 10 are pretensioned with respect to each other, see FIG. 1 and FIG. 6b. The force is directed such that, in use, the resilient element 14 exerts a force $F_1$ directed outwards on the upper leg via a lower pressure plate 16 of the upper leg engaging part 4, and a force $F_2$ directed inwards on the upper leg via an upper pressure plate 18 of the upper leg engaging part 4. It will be clear that, in this example, the force $F_1$ is thus directed transversely to the sagittal plane, in the lateral direction, and the force $F_2$ is thus directed transversely to the sagittal plane, in the medial direction. It will be clear that the resilient element 14 thus exerts moment on the upper leg engaging part 4 and consequently, in use, on the upper leg.

The moment exerted on the upper leg may, for instance, press the hip into its socket. In FIG. 1, the coupling part 10 is provided with a sleeve 20 which prevents an outward movement of an end 22 of the connecting part 8. Here, the end 22 of the connecting part 8 is slidably positioned in the sleeve 20 of the coupling part 10. Consequently, the resilient element 14 exerts a force $F_1$ directed outwards on the coupling part 10 via the end 22 in the point of contact 12. It will be clear that, in this example, the force $F_1$ is thus directed transversely to the sagittal plane, in the lateral direction, for instance along the virtual line 24. The sleeve 20 can be designed as a rigid element from, for instance, metal or plastic, but also as a flexible, elastic or resilient part from, for instance, rubber or (plastic) cloth.

In FIG. 1, the wearer of the orthosis is in a standing position. The point of contact 12 is then substantially at some distance above the point of rotation 25, and therefore above the line 24, see FIG. 4a. The lower and upper pressure plate 16 and 18, respectively, are substantially below the line 24. As a result, the resilient element 14 will effectively exert a force F and a moment M on the hip joint of the upper leg, which joint is located on line 24, while the force F is directed substantially inwards in the embodiment shown in FIG. 1. It will be clear that, in this example, the force F is thus directed transversely to the sagittal plane, in a medial direction, for instance along the virtual line 24. As a result, the hip is pressed into its socket, so that the risk of dislocation is reduced further. In the embodiment shown in FIG. 1, the moment M is directed such that the knee of the upper leg is pressed substantially outwards, in a direction transverse to the sagittal plane. As a result, too great an adduction of the upper leg (towards the other leg), which increases the risk of dislocation of the hip, can be prevented.

Figure 2:
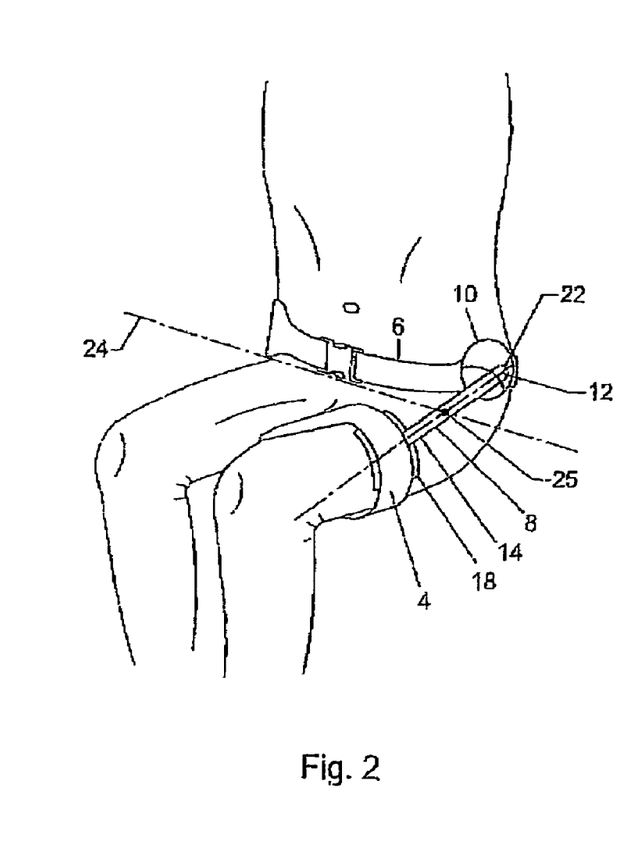
FIG. 2 shows a similar view to FIG. 1 when the wearer is sitting.

FIG. 2 shows the first exemplary embodiment with a person in a sitting position. FIG. 2 again shows the line 24 through the hip balls of the person. The hip orthosis 2 is designed such that the point of contact 12 can move with respect to the trunk engaging part 6 if the upper leg is moved relative to the trunk, see FIGS. 4a and 4b. In FIG. 2 and FIG. 4b, the point of contact 12 is substantially at some distance beyond the point of rotation 25, and therefore beyond the line 24, viewed from the front side of the person. The lower and upper pressure plate 16 and 18, respectively, are substantially in front of the line 24. Also in this sitting position, the resilient element 14 will effectively exert a force F and a moment M on the hip joint of the upper leg, which joint is located on the line 24, while the force F is substantially directed inwards. It will be clear that, in this example, the force F is thus directed transversely to the sagittal plane, in the medial direction. Thus, the hip is pressed into its socket, so that the risk of dislocation is reduced. In FIG. 2, the resilient element 14 will also exert the moment on the upper leg engaging part 4 and consequently, in use, on the upper leg. In the sitting condition shown in FIG. 2 and FIG. 4b, the point of contact 12 is located in different position with respect to the trunk from the position in the standing condition shown in FIG. 1 and FIG. 4a. In both cases, the point of contact 12 is located substantially at some distance beyond a point of rotation 25, located on the line 24 through the two hip balls of the person, viewed in a direction from the upper leg engaging part 4 towards the point of rotation 25. As a result, in both FIG. 1 and FIG. 2, the moment M is directed such that the knee of the upper leg is pressed substantially outwards, in a direction transverse to the sagittal plane.

Figure 3:
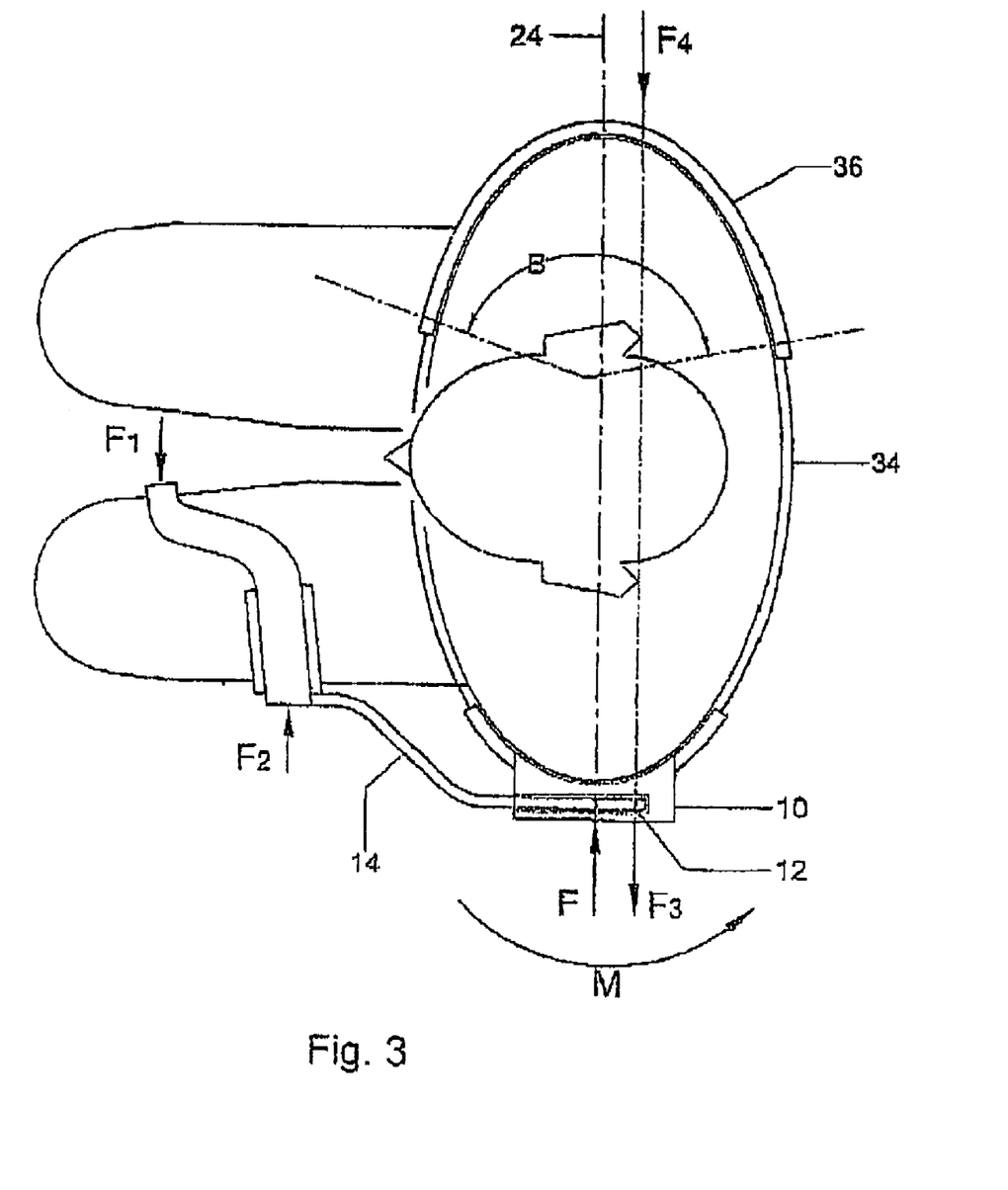
FIG. 3 shows a top plan view of the exemplary embodiment shown in FIG. 2.

FIG. 3 shows a top plan view of an embodiment of the orthosis 2 according to FIG. 1, with a sitting person. Therein, it is indicated that the force of the resilient element 14 preferably substantially engages the coupling part 10 in the point of contact 12, while the point of contact 12, viewed from the front side of the person, is located beyond the line 24 through the hip balls of the person. The resulting force $F_3$ exerted by the upper leg engaging part 4 on the coupling part 10, and therefore on the trunk engaging part 6, will therefore be located on the rear side of the person. By the trunk girding part 34, this force $F_3$ is guided from the trunk engaging part 6 along the trunk to the pressure area, which pressure area is located on the side 36 of the trunk facing away from the coupling part 10. The force $F_4$ resulting from force $F_3$ is also located on this side 36 of the person facing away from the coupling part 10. As a result, forces which act on the trunk engaging part can be supported on the trunk without the trunk engaging part having the tendency to twist.

The trunk girding part 34 may, for instance, be designed such that the trunk girding part 34 can substantially only absorb tensile forces in the circumferential direction of the trunk girding part 34, and cannot absorb forces ion a direction transverse to the trunk girding part 34. Preferably, at least a part of the trunk girding part 34 is integrally provided with a flexible and/or resilient material. Such material may, for instance, wholly or partly gird the respective part of the trunk. If the trunk girding part 34 has an at least partly resilient design, the trunk girding part 34 may also, for instance, contribute to a clamping force which keeps the trunk engaging part 6 positioned with respect to the trunk. If the trunk girding part 34 is provided with a flexible or resilient portion, the trunk girding part 34 forms a girding arc B around the trunk side 36 facing away from the coupling part, which girding arc makes it possible to absorb the resulting force $F_4$ on the rear side of the trunk.

Figure 4A:
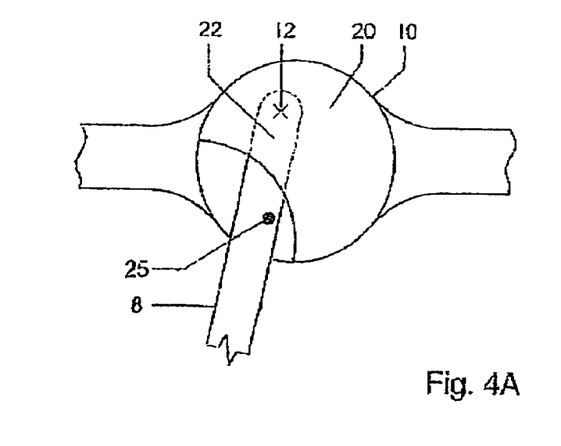
FIG. 4a shows a detail of the first exemplary embodiment in the position shown in FIG. 1.
Figure 4B:
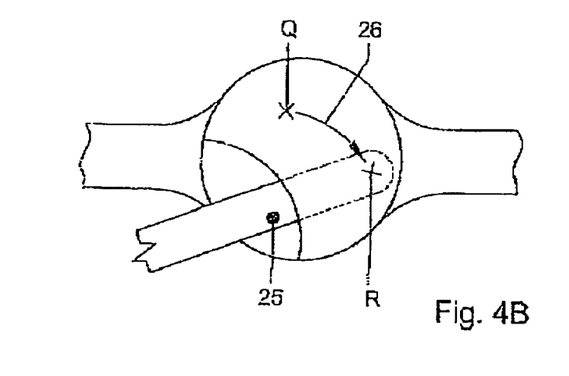
FIG. 4b shows a detail of the first exemplary embodiment in the position shown in FIG. 2.

FIG. 4a shows a side elevational view of a portion of the connecting part 8 and the coupling part 10 of the embodiment of the orthosis 2 from FIG. 1. Here, the parts are shown in the positions which they assume with respect to one another if the orthosis 2 has been fitted to a standing person. The hip orthosis 2 is arranged such that the connecting part 8 reaches beyond the point of rotation 25, viewed in the direction from the upper leg engaging part 4 towards the point of rotation 25. The end 22 having a rod-shaped design of the connecting part 8 is located in the sleeve 20 of the coupling part 10, which engages the end 22 of the connecting part 8 reaching beyond the point of rotation 25, and operatively prevents a movement of the rod-shaped end 22 in a direction directed away from the person (at least outwards, transverse to the sagittal plane). Then, the point of contact 12 is in a first position Q, in the top of the sleeve 20, viewed from the person, substantially above the point of rotation 25. When the person sits down, the situation is obtained as shown in FIG. 4b. Here, the point of contact 12 has shifted from the first position Q through a path 26 to a second position R, which is substantially located in the rear of the sleeve 20, substantially beyond the point of rotation 25 viewed from the front side of the person. In each position Q, R, the point of contact 12 is located at a distance from the point of rotation 25, and consequently the line 24, viewed in a direction from the upper leg engaging part 4 towards the point of rotation 25. Thus, in a simple and inexpensive manner, a force and a moment can be applied to the hip joint.

Figure 5A:
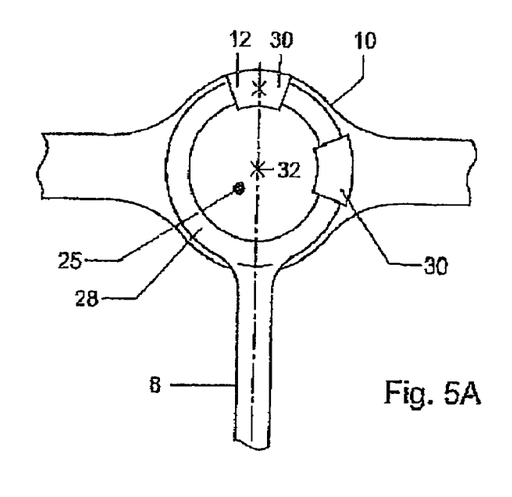
FIG. 5a shows a similar detail to FIG. 4a of a second exemplary embodiment.
Figure 5B:
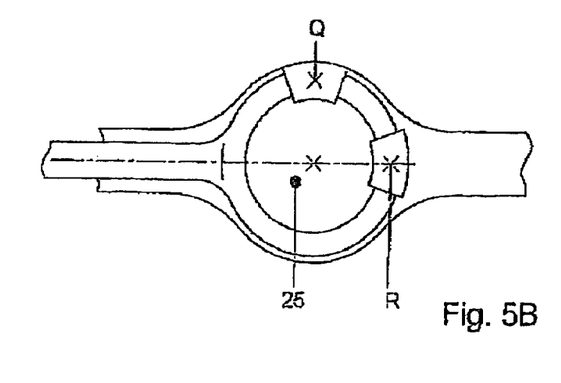
FIG. 5b shows a similar detail to FIG. 4b of a second exemplary embodiment.

FIG. 5a shows a side elevational view of a portion of the connecting part 8 and the coupling part 10 of a second embodiment of the orthosis 2. Here, the parts are shown in the positions which they assume with respect to one another if the orthosis 2 has been fitted to a standing person. The connecting part 8 is provided with an annular part 28, which is coupled to the trunk engaging part 6 by means of coupling loops 30 of the coupling part 10. The operation of the exemplary embodiment shown in FIGS. 5a and 5b is analogously to the operation of the exemplary embodiment shown in FIGS. 1-4. Here, the annular part rotates about a center 32, and a point of contact 12 shifts from the first position Q where the point of contact was located in the standing position to a second position R, see FIGS. 5a and 5b.

FIG. 6a shows the embodiment of the orthosis 2 according to FIG. 1, during fitting. The upper leg engaging part 4 has been fitted to the upper leg. The trunk engaging part 6 has not yet been fitted to the trunk. In this situation, the resilient element 14, designed as a leaf spring, is in untensioned condition and recedes away from the upper leg. FIG. 6b shows the embodiment of the orthosis 2 according to FIG. 1 which has been fitted completely to a standing person. The upper leg engaging part 4 has been fitted to the upper leg. The trunk engaging part 6 has been fitted to the trunk. In this situation, the resilient element 14 has been pulled through the sleeve 20 of the coupling part 10 to the trunk and is therefore in a tensioned condition substantially along the upper leg. The tensioned resilient element 14 exerts the force $F_1$ directed outwards on the upper leg via the lower pressure plate 16 of the upper leg engaging part 4, and the force $F_2$ directed inwards on the upper leg via the upper pressure plate 18 of the upper leg engaging part 4. The sleeve 20 prevents a movement directed outwards of the end 22 of the connecting part 8. The resilient element 14 consequently exerts the force $F_3$ directed outwards on the coupling part 10 via the end 22. In this manner, the orthosis 2 offers a great wearing comfort, while hip dislocation is prevented well.

Figure 7A:
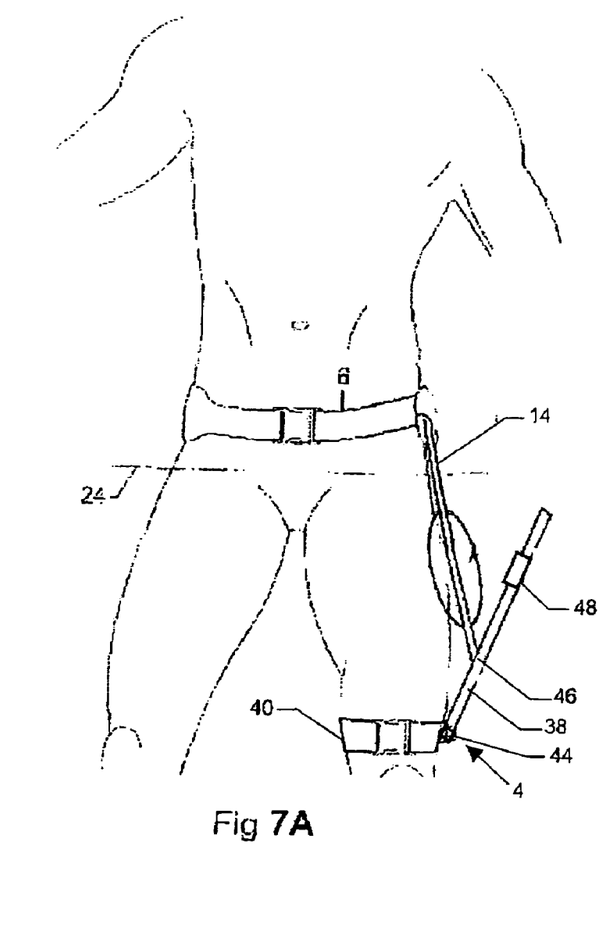
FIG. 7a shows a similar view to FIG. 1 of a third exemplary embodiment in untensioned condition.
Figure 7B:
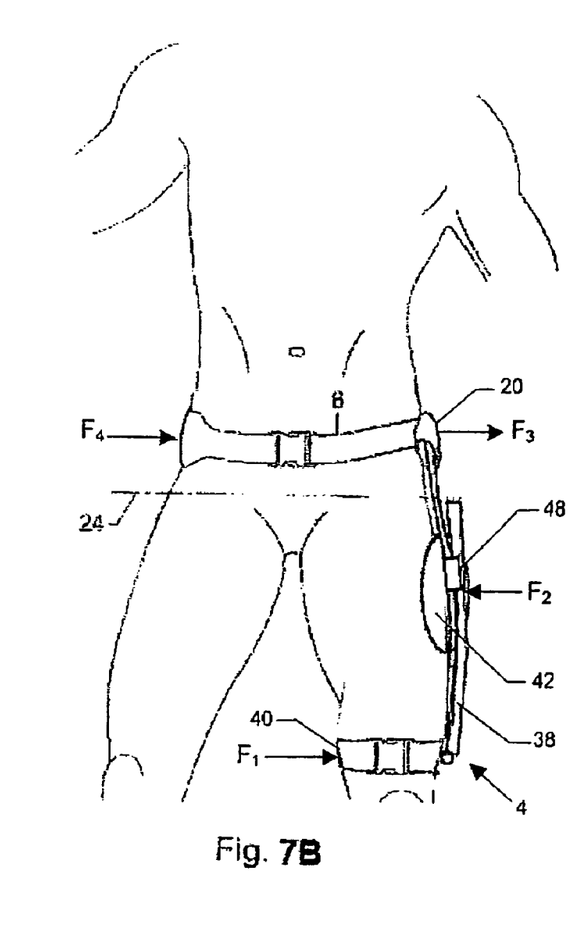
FIG. 7b shows the orthosis of FIG. 7a in tensioned condition.

FIGS. 7a and 7b show a third embodiment of the orthosis 2. In this example, the connecting part 8 is provided with a resilient element 14, comprising a leaf spring in the embodiment shown. In this example, the coupling part 10 is provided with the sleeve 20 which, operatively, prevents a movement directed outwards of the end 22 of the connecting part 8.

In FIGS. 7a and 7b, the upper leg engaging part 4 comprises a band 40 enclosing the upper leg. In this example, the upper leg engaging part 4 further comprises a lever 38. The lever 38 is hingedly connected or hingedly connectable with the band 40 in a first hinge point 44. In this example, the leaf spring is hingedly connected or hingedly connectable with the lever 38 in a second hinge point 46. In this example, the lever has a substantially rigid design and is, for instance, manufactured from plastic or metal.

The embodiment of the orthosis 2 shown in FIGS. 7a and 7b can be fitted to the user as follows.

FIG. 7a shows the third embodiment of the orthosis 2, during fitting. The upper leg engaging part 4 has been fitted to the upper leg. To this end, in this example, the band 40 has been fitted around the upper leg, for instance by closing a snap connection or buckle of the band. The trunk engaging part 6 has also already been fitted to the trunk. The end 22 of the connecting part 8, in this example the end of the leaf spring, can then be inserted into the sleeve.

It is also possible that the trunk engaging part 6 and upper leg engaging part 4 are, for instance, inseparably connected. To this end, for instance the connecting part 8 and the coupling part 10 can be connected, optionally inseparably, for instance by means of a snap connection. Here, the connecting part 8 and the coupling part 10 may, for instance, be connected such that the user cannot detach or is not allowed to detach the connection. In that case, the user will not insert the end 22 of the connecting part 8 into the sleeve 20, since the connecting part 8 has then already been connected with the coupling part 10. Here, it is possible that, for instance, an expert, such as a medical instrument maker, or another person who takes the user's measurements for the orthosis can and/or is allowed to detached the connection between the trunk engaging part 6 and upper leg engaging part 4. To this end, the connecting part 8 may, for instance, be connected with the coupling part 10 such that the connection is only detachable by utilizing a special tool or a key.

Since, in this example, the resilient element 14 is connected to the band 40 fitted to the upper leg via the second hinge point 46, the lever 38 and the first hinge point 44, inserting the end 22 into the sleeve 20 requires little force and/or effort, In this situation, the resilient element 14, designed as a leaf spring, is in an untensioned condition and recedes away from the upper leg. To this end, in an untensioned condition, the leaf spring may, for instance, trace an arc or comprise a bend. In this situation, the lever 38 is not excited and, in this example, recedes away from the upper leg and from the resilient element 14.

Then, the lever 38 can be tilted about the first hinge point 44, so that the lever 38 is moved towards the upper leg. Here, the second hinge point 46 will be moved towards the upper leg, and the leaf spring will be tensioned. The resilient element 14 is thus in the tensioned condition substantially along the upper leg, see FIG. 7b. As soon as the resilient element 14 has been tensioned, the lever 38 and the resilient element can be fixed with respect to each other, so that the tensioned condition of the resilient element 14 is maintained. In this example, to this end, the lever 38 is provided with fixing means 48, for instance a snap connection, which engage the resilient element 14. Preferably, the lever 38 and the resilient element 14 are fixed with respect to each other such that the fixation cannot be broken by accident, at least is difficult to break by accident. To this end, the snap connection may, for instance, be provided with an operating element which is to be operated with at least two fingers.

It will be clear that, by using the lever 38 for tensioning the resilient element 14, it is simpler to fitting the orthosis 2 to the user, since less force needs to be exerted for tensioning the resilient element 14.

As can seen in FIG. 7b, the tensioned resilient element 14 exerts the force $F_1$ directed outwards on the upper leg via the band 40 of the upper leg engaging part 4, and the force $F_2$ directed inwards on the upper leg via a pressure piece 42 of the upper leg engaging part 4 connected with the resilient element 14 in this example. The sleeve 20 prevents a movement directed outwards of the end 22 of the connecting part 8. The resilient element 14 thus exerts the force $F_2$ directed outwards on the coupling part 10 via the end 22.

In FIGS. 7a and 7b, the resilient element 14 is hingedly connected or hingedly connectable with the lever 38 in the second hinge point 46. It will be clear that it is also possible that the connecting part 8 is provided with a, for instance, at least partly substantially rigid sub-connecting part which is hingedly connected or hingedly connectable with the lever 38 in the second hinge point 46, while the sub-connecting part further comprises the resilient element 14. The sub-connecting part may, for instance, comprise a substantially rigid rod or strip which comprises a leaf spring near the end directed towards the coupling part 10.

The invention is by no means limited to the embodiments shown in the Figures. Various modifications are possible within the framework of the invention as set forth in the following claims.

Thus, it is, for instance, possible that the coupling part is provided with at least one resilient element. Also, the connecting part may be provided with more than one resilient element.

In one alternative embodiment, the connecting part is designed as a substantially rigid element which is hingedly connected with the upper leg engaging part. Here, if only the upper leg engaging part has been fitted to a person, the connecting part can recede away from the upper leg under the influence of a spring force provided by a, resilient element, for instance a coil spring or a piece of elastomer. The trunk engaging part can then be designed in accordance with the embodiment shown in FIG. 1.

In another alternative embodiment, the upper leg engaging part is completely designed as a rigid part. In this case, the coupling part may, for instance, be designed as a sleeve or shell which is connected with the trunk engaging part by means of a resilient element in order to exert a force and/or moment on the hip joint via the upper leg engaging part in use.

In a further alternative embodiment, both the connecting part and the coupling part comprise a rigid bracket between which a resilient element, for instance a draw spring or compression spring, elastic, etc., is tensioned. Here, the resilient element is positioned such that the element exerts a force on the connecting part and the coupling part along a line of force, which line of force is operatively substantially located at some distance from the line through the two hip balls of the person, and which line of force, in neutral position, runs substantially parallel to the line through the two hip balls. If the upper leg is moved relative to the trunk, the direction of the line of force will also vary with respect to the line through the two hip balls.

Further, the upper leg engaging part may be connected with the trunk connecting part via at least two, preferably three, hinges, whose axes of rotation run substantially parallel to the line through the two hip balls. Thus, the upper leg engaging part can hinge and translate with respect to the trunk engaging part so that the risk of twisting of the trunk engaging part around the trunk is reduced, while the freedom of movement of the upper leg remains is limited to the substantially forward and backward directions. Here, for instance, the upper leg engaging part may be connected with the connecting part via resilient element, in order to apply a force and/or moment to the hip joint.

The at least one resilient element mentioned may be designed in different manners and comprise, for instance, a leaf spring, torsion spring, draw spring, compression spring, gas spring, elastic material and/or the like.

Such variants are all understood to fall within the framework of the invention.

The invention claimed is:

1. A hip orthosis, comprising:
a trunk engaging part;
an upper leg engaging part;
a coupling device intercoupling the trunk engaging part to the tipper leg engaging part, the coupling device having at least one resilient element for operatively preventing an adducting movement of an tipper leg engaged by the upper leg engaging part by a spring force,
the coupling device comprising a connecting part connected to the upper leg engaging part and a coupling part connected to the trunk engaging part, wherein, during use, the connecting part is rotatable about a point of rotation with respect to the coupling part, wherein the point of rotation is defined as a virtual point of rotation;
wherein the resilient element is defined as a leaf spring;
wherein the at least one resilient element exerts a pressing force on a hip joint, such that a hip is pressed into a socket thereof under the influence of the pressing force.

2. The hip orthosis according to claim 1, wherein the force is directed substantially inwards toward the wearer.

3. The hip orthosis according to claim 1, wherein the at least one resilient element exerts a moment on the hip joint.

4. The hip orthosis according to claim 1, wherein the at least one resilient element exerts a moment on the hip joint.

5. The hip orthosis according to claim 4, wherein the moment is directed such that the upper leg is rotated substantially outwards, in a direction transverse to the sagittal plane.

6. The hip orthosis according to claim 1, wherein the trunk engaging part is arranged such that a point of rotation is located on a line which generally intersects two hip balls of a wearer of the orthosis.

7. The hip orthosis according to claim 1, wherein the connecting part and the coupling part are pretensioned with respect to each other.

8. The hip orthosis according to claim 7, the resilient element exerts a force directed outwards on the coupling part.

9. The hip orthosis according to claim 1, wherein when the upper leg engaging part is fitted to the upper leg, the leaf spring is arranged to move away from the upper leg in an untensioned condition, and is located substantially along the upper leg in a tensioned condition.

10. The hip orthosis according to claim 1, wherein the hip orthosis includes a lever arranged to move the at least one resilient element into a tensioned condition.

11. The hip orthosis according to claim 10, wherein the hip orthosis is provided with a fixing device arranged to fix the lever and the at least one resilient element with respect to each other to maintain the at least one resilient element in the tensioned condition.

12. The hip orthosis according to claim 1, wherein the connecting part and the coupling part engage each other at least in a point of contact, which point of contact is arranged to operatively move with respect to the trunk engaging part if the upper leg is moved relative to a trunk.

13. The hip orthosis according to claim 12, wherein the point of contact is located at a distance from the point of rotation.

14. The hip orthosis according to claim 13, wherein both in standing and in sitting condition, the point of contact is located beyond the point of rotation, viewed in a direction from the upper leg engaging part towards the point of rotation.

15. The hip orthosis according to claim 1, wherein the connecting part reaches beyond the point of rotation viewed in a direction from the upper leg engaging part towards the point of rotation.

16. The hip orthosis according to claim 15, wherein both in a standing and in a sitting condition, the connecting part reaches beyond the point of rotation, viewed in a direction from the upper leg engaging part towards the point of rotation.

17. The hip orthosis according to claim 15, wherein the coupling part engages at least the portion of the connecting part reaching beyond the point of rotation, with different rotational positions of the connecting part.

18. The hip orthosis according to claim 1, wherein the connecting part is slidably coupled to the coupling part.

19. The hip orthosis according to claim 14, wherein the connecting part comprises a rod-shaped end, wherein the coupling part is arranged for operatively preventing an outward movement of the rod-shaped end with respect to the trunk engaging part.

20. The hip orthosis according to claim 19, wherein the coupling part is provided with a sleeve for, operatively, at least partly receiving the rod-shaped end therein.

21. The hip orthosis according to claim 15, wherein the connecting part comprises an annular part, wherein the coupling part is arranged for operatively preventing an outward movement of the annular part with respect to the trunk engaging part.

22. The hip orthosis according to claim 1, wherein the trunk engaging part is provided with a trunk girding part arranged for girding a part of a trunk of a wearer wherein the trunk girding part is arranged for guiding a force ($F_3$) coming from the coupling device to a trunk side facing away from the coupling device.

23. The hip orthosis according to claim 22, wherein the trunk girding part is arranged for substantially only absorbing tensile forces in the circumferential direction of the trunk girding part.

24. The hip orthosis according to claim 23, wherein the girding part includes a flexible or resilient material.

25. A method for preventing the dislocation of a hip of a person, comprising the steps of attaching a trunk engaging part to the trunk of a wearer;

attaching an tipper leg engaging part to the upper leg of a wearer;

intercoupling the trunk engaging part with the upper leg engaging part by connecting a connecting part with the upper leg engaging part and connecting a coupling part with the trunk engaging part;

operatively preventing an adducting movement of an upper leg engaged by the upper leg engaging part with a spring force provided by at least one resilient element having a leaf spring;

responsive to movement of the person, rotating the connecting part about a point of rotation with respect to the coupling part, wherein said point of rotation is a virtual point of rotation; and preventing an inward movement of the associated tipper leg by a spring force;

wherein the force is directed substantially such that the hip is pressed into its socket under the influence of that force.

26. The method according to claim 25, wherein the force is directed substantially inwards.

27. The method according to claim 25, wherein the upper leg is rotated substantially outwards, in a direction transverse to the sagittal plane, by a moment.

* * * * *

UNITED STATES PATENT AND TRADEMARK OFFICE
CERTIFICATE OF CORRECTION

PATENT NO. : 7,597,672 B2 Page 1 of 1
APPLICATION NO. : 11/438474
DATED : October 6, 2009
INVENTOR(S) : Lambertus Joseph Martinus Kruijsen It is certified that error appears in the above-identified patent and that said Letters Patent is hereby corrected as shown below:

Column 9, in claim 1, line 40, replace "tipper" with --upper--;

Column 9, in claim 1, line 42, replace "tipper" with --upper--;

Column 11, in claim 25, line 6, replace "tipper" with --upper--;

Column 12, in claim 25, line 5, replace "tipper" with --upper--.

Signed and Sealed this

Twenty-fourth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,597,672 B2  Page 1 of 1
APPLICATION NO. : 11/438474
DATED : October 6, 2009
INVENTOR(S) : Kruijsen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 452 days.

Signed and Sealed this

Twenty-eighth Day of September, 2010

David J. Kappos
*Director of the United States Patent and Trademark Office*